United States Patent [19]

Eggers

[11] Patent Number: 4,946,439
[45] Date of Patent: Aug. 7, 1990

[54] DUAL SOURCE PARENTERAL INFUSION SYSTEM WITH SECONDARY INFUSION MODULE

[75] Inventor: Philip N. Eggers, San Jose, Calif.

[73] Assignee: Critikon, Inc., Tampa, Fla.

[21] Appl. No.: 232,058

[22] Filed: Aug. 15, 1988

[51] Int. Cl.$^5$ .............................................. A61M 5/16
[52] U.S. Cl. ........................................ 604/67; 604/65; 604/81; 604/245; 128/DIG. 13
[58] Field of Search .................. 604/50, 65, 67, 80, 604/81, 245; 128/DIG. 13

[56] References Cited

U.S. PATENT DOCUMENTS

| | | | |
|---|---|---|---|
| 3,886,937 | 6/1975 | Bobo et al. | 604/80 |
| 3,982,534 | 9/1976 | Buckman | 604/80 |
| 4,094,318 | 6/1978 | Burke et al. | 604/81 |
| 4,114,617 | 9/1978 | Turner et al. | 604/80 |
| 4,300,552 | 11/1981 | Cannon | 604/65 |
| 4,314,567 | 2/1982 | Cannon | 604/30 |
| 4,553,347 | 8/1985 | Deckert | 604/81 |
| 4,553,958 | 11/1985 | Le Colq | 604/81 |
| 4,576,592 | 3/1986 | Danby | 604/80 |
| 4,637,817 | 1/1987 | Archibald et al. | 604/81 |
| 4,710,166 | 12/1987 | Thompson et al. | 604/81 |
| 4,821,028 | 4/1989 | Deckert et al. | 604/67 X |

Primary Examiner—John D. Yasko
Assistant Examiner—C. Maglione
Attorney, Agent, or Firm—W. Brinton Yorks, Jr.; Paul A. Coletti

[57] ABSTRACT

A dual source parenteral infusion system includes a primary controller which controls the flow rate of a parenteral solution, a display which displays parameters associated with the delivery of a primary solution, and pushbuttons for entering solution delivery parameters into the controller. The primary controller communicates with a secondary infusion module which is programmed to deliver solution from a secondary source, with the flow rate being controlled by the primary controller. The secondary infusion module includes a display for displaying parameters associated with the delivery of the secondary solution and a drop detector, and mounts about a drip chamber for the secondary solution. The module may also include pushbuttons for entering fluid delivery parameters for the secondary solution into the module.

15 Claims, 5 Drawing Sheets

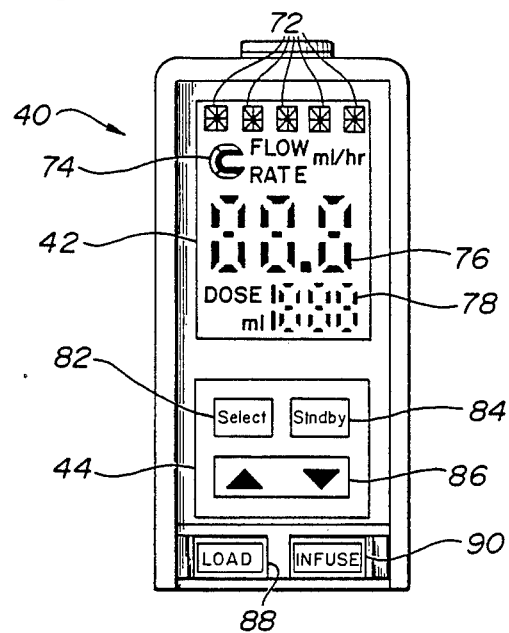
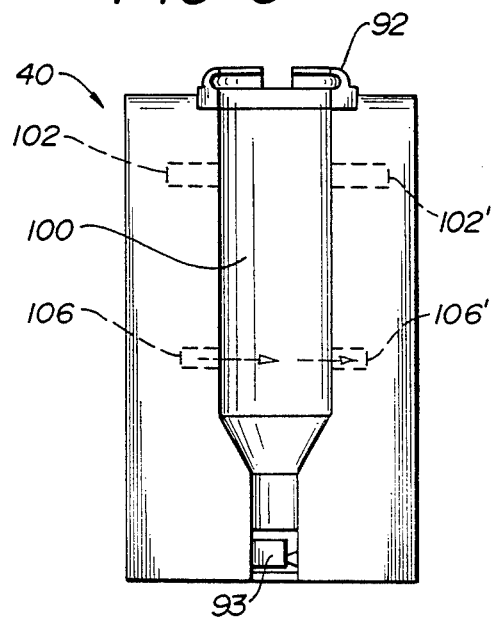
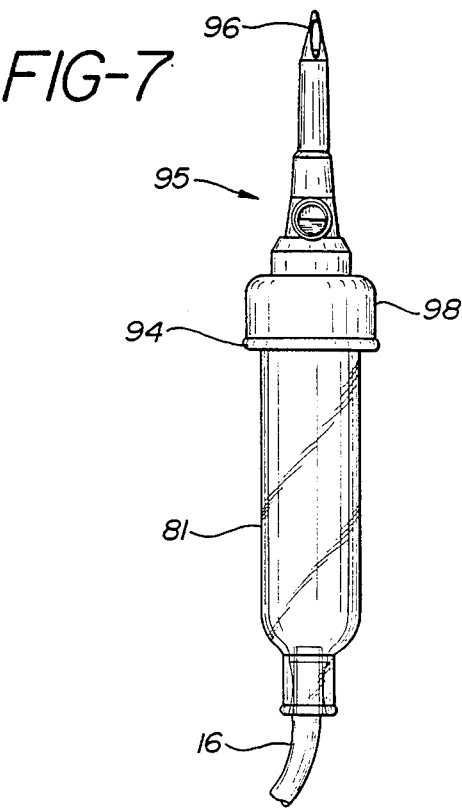

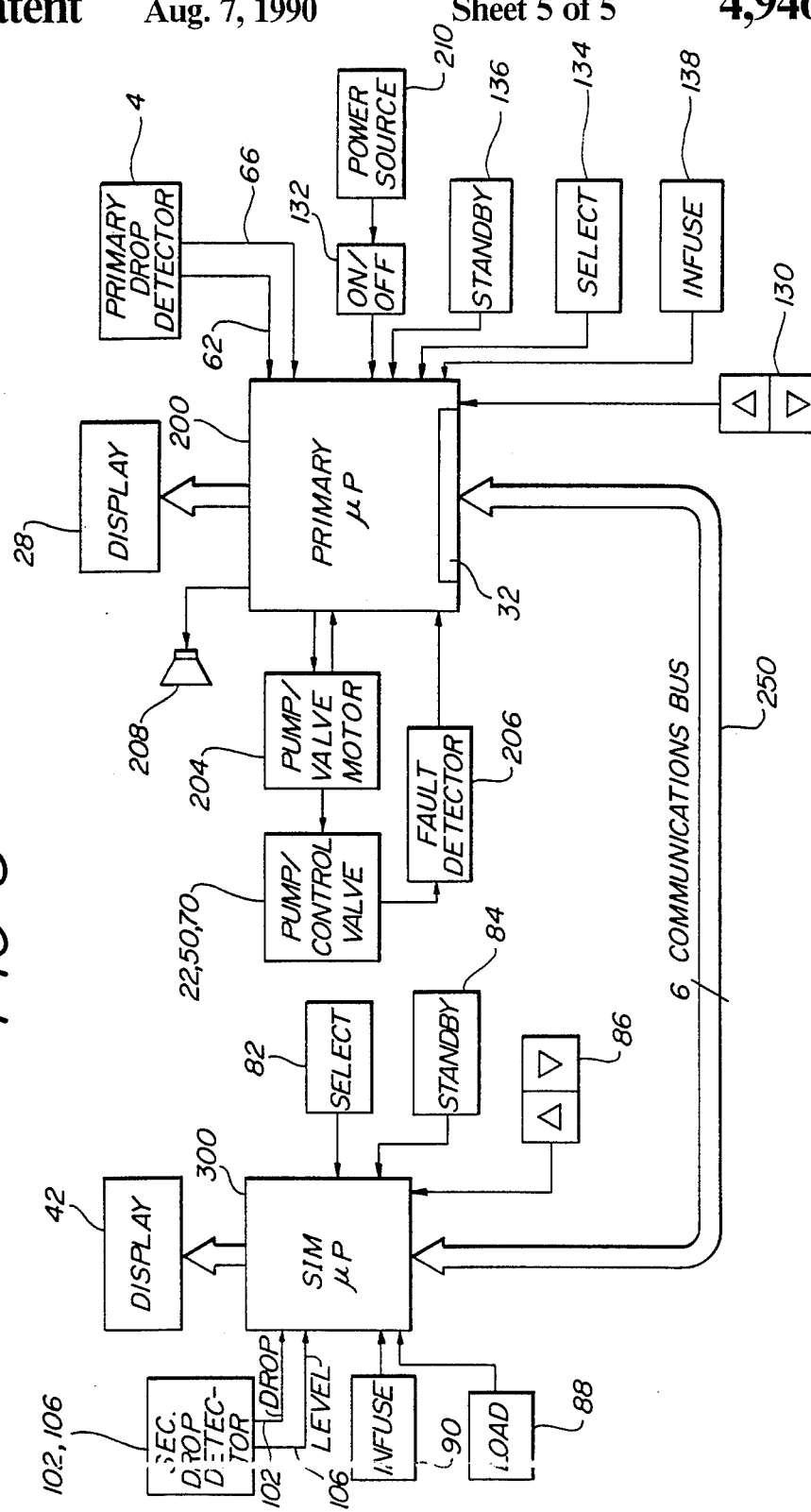

DUAL SOURCE PARENTERAL INFUSION SYSTEM WITH SECONDARY INFUSION MODULE

This invention relates to infusion systems which control the delivery of two sources of parenteral solutions to a patient and, in particular, to apparatus for monitoring and controlling the solutions being delivered in these systems.

Systems for delivering predetermined volumes of two parenteral solutions at predetermined flow rates have been known for a number of years. On such system is shown in U.S. Pat. No. 4,576,592. In that system, a primary administration tubing set and a secondary administration tubing set are joined at a "Y" connector and connected through a common conduit to a drip chamber on the primary controller. Below the drip chamber is a precision flow control valve for regulating the flow of solution through the common conduit. A second driP chamber in the secondary administration set is monitored by a drop detector which is electrically connected to the primary controller. Parenteral solution is initially supplied by the secondary solution source, and its delivery is monitored by the drop detector and its flow is controlled by the control valve. When delivery of the secondary solution is completed a pinch valve on the controller occludes the secondary tubing set and solution begins to flow from the primary source. The delivery of primary solution is monitored by a drop detector and drip chamber on the primary controller, and its flow is controlled by the control valve. A check valve in the primary administration set prevents flow of the primary solution while the secondary solution is being delivered.

U.S. Pat. No. 4,533,347 shows a similar system in which the drip chamber for the primary solution is located in the primary administration set. The drop detector for the primary solution is located about this drip chamber, remote from the primary controller. Thus, each administration set includes a drip chamber and an associated drop detector. Operation of the system is as described for the '592 patent.

U.S. Pat. No. 4,637,817 shows a dual source infusion system in which each administration set passes through a sequenced pinch valve above the Y-connector. The pinch valve alternately opens one of the tubing sets and closes the other, and the flow of parenteral solution is controlled by a pump located on the controller. The use of the sequenced pinch valve obviates the need for a check valve in the primary solution line, since the valve permits the flow of only one solution at a time.

Dual source administration systems are also shown in U.S. Pat. Nos. 3,886,937; 3,982,534; 4,094,318; 4,114,617; and 4,300,552.

The prior art systems described above are all similar in one respect. To initialize the system prior to fluid delivery, a user must enter flow rate and total dose values into the primary controller. As the values are entered, they are displayed on the primary controller display. The values for the two solution sources are separately entered and displayed. That is, the user first enters the values for one solution source and observes their entry on the display. The display is then cleared, and the user enters and observes the values for the other solution source. During operation of the system, the delivery rate and volume of the solution being delivered at that time are viewed on the display.

With only a single set of value entry controls it is at times confusing for the user to be certain that the values being entered are associated with the proper solution. It would be desirable to provide an unambiguous way of entering the values for fluid delivery for the two solution sources. Moreover, with only a single display, it is often confusing to discern which source is delivering fluid, and what the state is of the other source. It would be desirable for a user to be able to discern at a glance which source is delivering fluid at any point in time. It would further be desirable to be able to quickly ascertain the delivery state of both solutions. For instance, when the delivery of fluid from the second source has ended and the delivery of primary solution has commenced, a nurse should be able to immediately note both the progress of secondarY solution delivery and the dose previously delivered from the primary source without manipulating the system or interrupting the flow of primary solution.

In accordance with the principles of the present invention, a dual source parenteral infusion system is provided which enables a user to unambiguously control and monitor the delivery of the two solutions. The primary controller of the system includes means for controlling the rate of fluid delivery, means for entering values for controlling the delivery of the primary solution, and a display for displaying both the entry of the primary solution delivery values and the progress of primary solution delivery. A secondary infusion module communicates with the primary controller and is adapted for coupling to the secondary administration set. The secondary infusion module includes means for monitoring the delivery of secondary solution, and a display for displaying the progress of secondary solution delivery. Thus, the secondary infusion module provides a display which is unambiguously located in proximity to the secondary administration set.

In a preferred embodiment, entry of the secondary solution delivery values is provided at the secondary infusion module. The user can visually ascertain the parameters for secondary solution delivery directly on the display of the secondary infusion module. The secondary infusion module also includes means for opening and occluding a conduit in the secondary administration set as infusion of the secondary solution commences and terminates.

In the drawings:

FIGS. 5 and 6 illustrate the secondary infusion module of the infusion system of FIG. 1;

FIG. 7 illustrates a spike and drip chamber suitable for use in the secondary administration set with the secondary infusion module of FIGS. 5 and 6; and FIG. 8 illustrates in block diagram form the location and interaction of control functions in the infusion system of FIG. 1.

Figure 1:
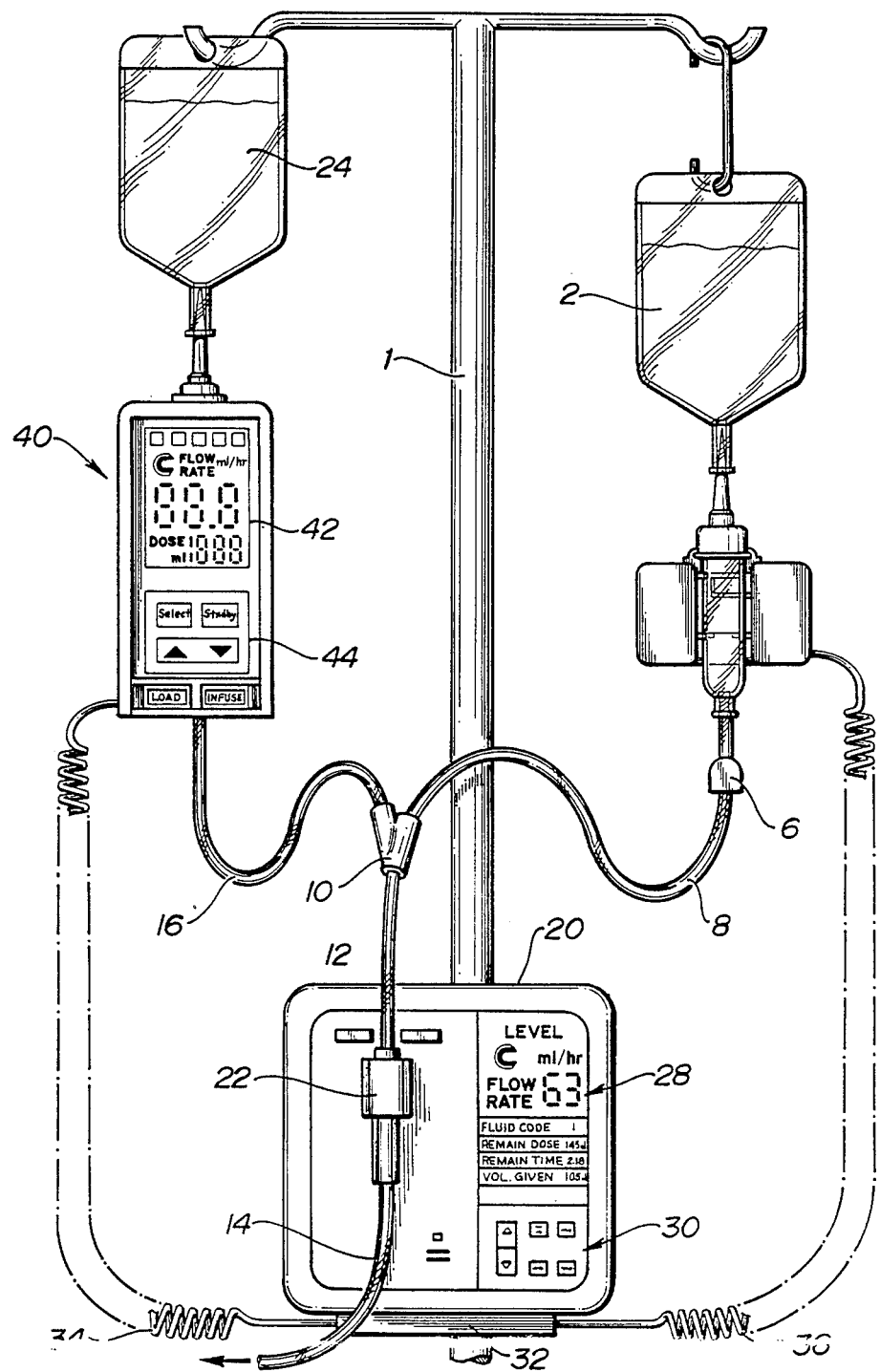
FIG. 1 illustrates a dual source parenteral infusion system constructed in accordance with the principles of the present invention.

Referring first to FIG. 1, a dual source parenteral infusion system constructed in accordance with the principles of the present invention is shown. A source 2 of a primary solution is suspended from a pole 1. The primary solution is delivered to a drip chamber 26, about which is mounted a drop detector 4. Tubing 8 of a primary solution administration set leads from the drip chamber to a Y-connector 10, and includes an in-line one-way check valve 6. The outlet of the Y-connector is connected by common tubing 12 to a precision control valve 22, which is mounted on a primary controller 20. An outlet tubing line 14 leads from the control valve 22 to the infusion site.

On the right-hand side of the front of the primary controller 20 is a display 28, which displays values indicating the progress of infusion of the primary solution. Below the display 28 is a group of pushbutton controls 30 for entry of values for controlling infusion of the primary solution. As the values are entered prior to operation of the system they may be viewed on the display 28. At the bottom of the central controller 20 is an interface box 32, which connects the primary controller to the drop dectector 4 and to a secondary infusion module 40 by way of cables 34 and 36.

Also suspended from the pole 1 is a secondary solution source 24. Tubing 16 of a secondary administration set connects the secondary solution supply to a second input port of the Y-connector 10. Located just below the secondary solution source 24 is a second drip chamber. This drip chamber is not visible in FIG. 1, as it is located inside the secondary infusion module 40. The secondary infusion module mounts around the second drip chamber in the same manner as the drop detector 4 mounts around drip chamber 26. The secondary infusion module includes a display area 42 which displays parameters indicating the progress of delivery of the secondary solution. Below the display area is a group of pushbutton controls 44. These controls permit entry of the values governing delivery of the secondary solution directly at the secondary infusion module. As the values are entered they may be visually ascertained directly on the display 42. One of the two pushbuttons at the bottom of the secondary infusion module controls an internal mechanism which opens and occludes the tubing line 16 as it passes through the secondary infusion module. The other pushbutton is depressed to begin infusion of the secondary fluid.

Figure 2A:
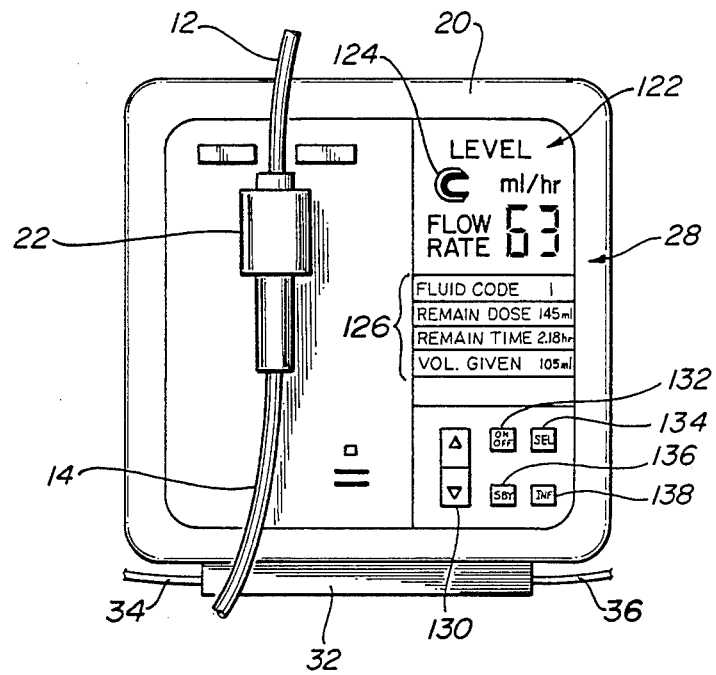
FIGS. 2a–2c illustrate primary controllers suitable for use in the infusion system of FIG. 1.

Turning now to FIG. 2a, a primary controller 20 is shown. On the right-hand side of the front of the controller 20 is a display 28. At the top of the display is an eight character message center 122, which displays error and other status messages. The individual characters in the message are each comprised of fourteen individually controlled segments to form the desired alphanumeric characters. Below and to the left of the message center is an instrument logo design 124 which pulses when the primary controller is operating. Below the logo design are three large numbers which indicate the flow rate in ml/hr at which the primary controller is currently operating. To the left of the numbers is the descriptor "FLOW RATE," and above the numbers are the units of ml/hr.

Below the indicated flow rate are four other lines of information concerning the primary infusion. The top line represents a fluid code which a user may enter to specify the type of solution being administered. The next line specifies the dose remaining to be delivered of the total dose programmed into the controller at the beginning of the procedure. The third line specifies the remaining time for completion of the administration of the programmed dose, and the fourth line indicates the volume of the programmed dose already administered.

Below the display are a number of pushbuttons used to start and stop the controller and the administration of fluid, and for programming the controller for the proper fluid administration. The up/down pushbuttons 130 are used to increment or decrement a value during programming of the controller. Pushbutton 132 is used to turn the controller off or on. The "SELECT" pushbutton 134 is used to select a value which is to be programmed into the controller, such as "dose" or "flow rate." The "SELECT" pushbutton may also be used to change values during fluid delivery by holding the "SELECT" pushbutton down while incrementing or decrementing a value with the up/down pushbuttons. Pushbutton 136 is depressed to stop the administration of solution, and pushbutton 138 is depressed to start fluid administration in accordance with the values programmed into the controller.

The control valve 22 shown in FIG. 2a is a precision pinch valve which encloses tubing line 12, 14, and is described in greater detail in U.S. Pat. No. 4,559,045. Inside the pinch valve the tubing is engaged between a movable pressure plate and a stationary pressure plate. A precision motor-driven actuator projects from the front of the controller and is in contact with the movable pressure plate to controllably move the movable pressure plate toward and away from the interposed tubing. The tubing is thereby selectively occluded to control the rate of flow of fluid through the outlet tubing 14.

Figure 2B:
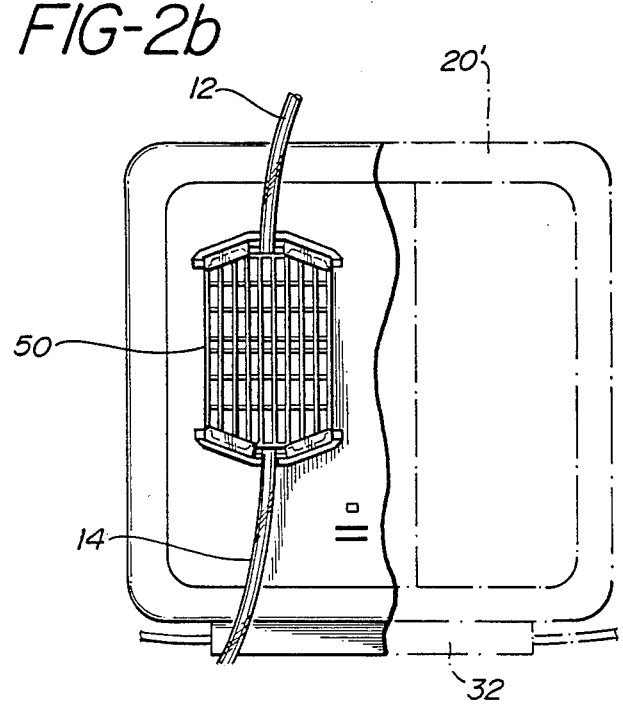

In the controller 20' of FIG. 2b the precision control valve 22 of FIG. 2a is replaced with a pump cassette which is in-line between the common tubing section 12 and the outlet tubing section 14. A diaphragm on the back of the cassette is controllably moved in and out by a pump actuator extending from the front of the controller. This pump cassette and its operation are more particularly described in U.S. patent applications No. 902,616, filed Sept. 2, 1986 and No. 25,681, filed Mar. 13, 1987.

Figure 2C:
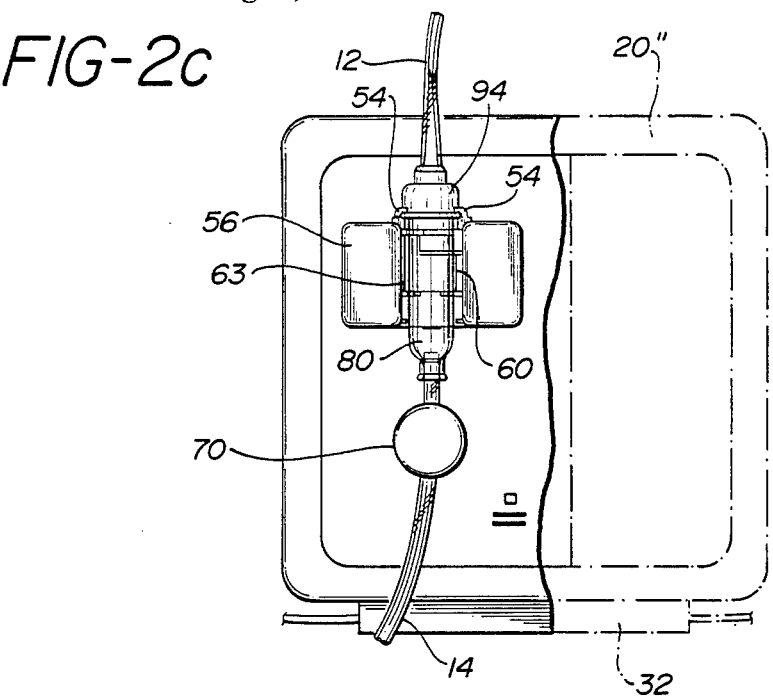

In the controller 20" of FIG. 2c the flow control mechanism shown is that used in the aforementioned U.S. Pat. No. 4,576,592. In this arrangement a drip chamber 80 has a cap 98 with an integrally molded drop former. A lip 94 at the bottom of the cap snaps into a retaining ring 54 at the top of a drop detector 56. When the drip chamber is properly located within the drop detector 56, its presence is detected by a door 60 which is hinged as indicated at 63. Falling drops within the drip chamber are detected by the optical path indicated by the arrows at the top of the chamber and their passage is use by the primary controller to measure the flow of primary solution. A precision pinch valve 70 below the drip chamber 80 selectively occludes the outlet tubing 14 to regulate the flow of parenteral solution to the patient. When the primary controller 20" of FIG. 2c is used in the system of FIG. 1, the primary drip chamber 26 and drop detector 4 can be dispensed with, as their function is provided by the drop detector 56 and drip chamber 80.

Figure 3:
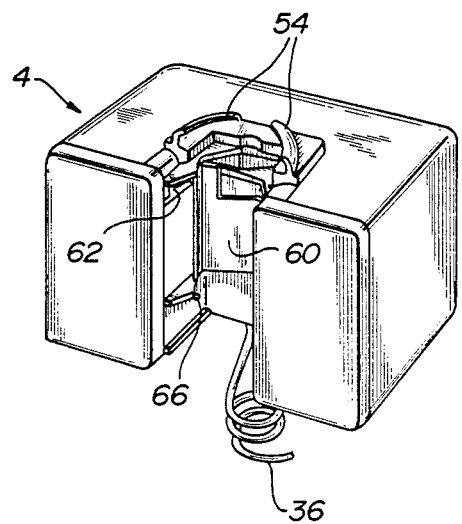
FIG. 3 illustrates a drop detector suitable for use with the primary drip chamber in FIG. 1.
Figure 4:
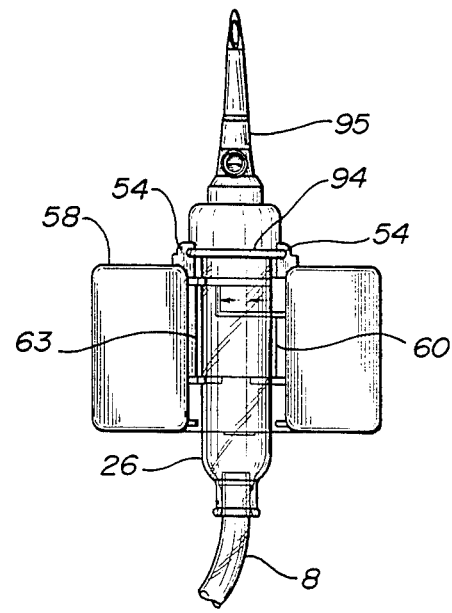
FIG. 4 illustrates the drop detector of FIG. 3 when mounted on the primary drip chamber.

The drop detector 4 and the drip chamber 26 of FIG. 1 are shown in detail in FIGS. 3 and 4. In FIG. 3 the drop detector 4 is seen to comprise a housing which encloses photodiodes and photodetectors for an optical drop detector 62 and an optical level detector 66. A spring hinged door 60 is located within the cavity in the center of the housing and projects forward in the absence of a drip chamber in the housing, in which position it blocks the optical path of the drop detector 62. At the top of the housing is a split mounting ring 54.

The drop detector 4 is mounted about the driP chamber 26 in FIG. 4 by snapping the lip 94 of the spike 95 at the top of the chamber into the mounting ring 54. The spike 95 is inserted into a parenteral solution bag or membrane in the cap of the suspended fluid source prior to mounting the drop detector. When the drip chamber 26 is properly engaged in the cavitY of the drop detector housing, the chamber presses the hinged door 60 to the rear of the cavity, thereby unblocking the optical path of the drop detector 62. The drop detector is able to sense the proper mounting of the drip chamber by the deflection of the door 60, and also senses proper priming of the drip chamber by the obscuring of the level detector 66 with fluid while the optics of drop detector 62 are unobscured. During normal operation, droplets will fall from the drop former and be detected by the optical drop detector 62. A detailed description of the drop detector 4 is presented in U.S. patent application SN 117,009, filed Nov. 4, 1987.

The secondary infusion module of the present invention is shown in the front and back views of FIGS. 5 and 6. At the top of the module 40 is a display 42, shown in FIG. 5. A five character message center 72 is located at the top of the display. These fourteen segment characters display alarm and status conditions during the administration of the secondary solution. Below the message center is an instrument logo design 74 which pulses during delivery of the secondary solution. Below the logo are three large characters 76 which display the flow rate of the solution. The descriptor "FLOW RATE" and the flow units of ml/hr are displayed above the flow rate numerals. Below the flow rate are three and one-half characters 78 which display the dose being administered, together with the descriptor "DOSE" and the units of ml.

Below the display 42 are a series of pushbuttons 44, which are used to program and operate the module 40. The "SELECT" pushbutton 82 is depressed to program the module. When this pushbutton is depressed, the descriptor and units of the value being entered flash on the display, and the value is incremented or decremented by depressing the up/down pushbuttons 86. The "STANDBY" pushbutton 84 is depressed to stop the administration of the secondary solution and start the administration of the primary solution, or to clear the alarms on the secondary infusion module. Below the pushbuttons 86 is a "Load" key 88, which is depressed while mounting the secondary infusion module around the secondary drip chamber. An "Infuse" key 90 is depressed to begin the administration of the secondary solution.

The side of the secondary infusion module is shown in FIG. 6. A cavity 100 in the module is accessible from the side for insertion of the secondary drip chamber shown in FIG. 7. At the top of the module is a mounting ring 92, similar to the mounting ring 54 of the drop detector 4. The secondary infusion module is mounted around the secondary drip chamber 81 by inserting the lip 94 of the drip chamber spike 95 into the mounting ring 92. When so engaged, the drip chamber 81 is positioned in the optical path of a drop detector 102, 102', and in the optical path of a low level detector 106, 106'. To properly engage the drip chamber in the cavity 100 a barrier 93 must be withdrawn from the bottom of the cavity 100. The barrier is withdrawn by depressing the "Load" key, whereupon the tubing section 16 is located in the passage at the bottom of the cavity. When the "Load" key is released the barrier 93 pinches the tubing section 16 closed. Fluid flow is thereby prevented until the "Infuse" key is depressed at the commencement of secondary infusion.

Control of the dual source infusion system of FIG. 1 is provided by two microprocessors, one located in the primary controller and another in the secondary infusion module, as shown in block diagram form in FIG. 8. The microprocessor 200 in the primary controller 20 interacts with other components of the primary controller as shown in the FIGURE. The microprocessor 200 activates and controls the display 28 and an alarm 208. It also controls a motor 204 for the pump or control valve, which in turn is connected to the pump or valve. Fault detector electronics 206 monitors the operation of the pump or valve and informs the microprocessor 200 of the pump or valve operation. Faults detected by the electronics 206 are conditions related to flow, such as slow flow, no flow, or an occlusion at the infusion site. When any of these conditions are detected, the microprocessor 200 will verify them and sound the alarm 208 and cease system operation until the alarm condition is remedied.

The primary microprocessor 200 receives information on primary solution drop detection from the primary drop detector 4 which may indicate an alarm condition, such as high or low solution level in the primary drip chamber, no drops, or a continuous stream of drops. Whenever any of these conditions are detected the microprocessor 200 will verify the problem, activate the alarm and cease system operation.

The primary controller 20 is initially turned on by closure of the on/off switch 132, which connects the microprocessor and other electronics to a power source 210. The microprocessor 200 also receives inputs from the standby pushbutton 136, the SELECT pushbutton 134, the infuse pushbutton 138, and the up/down pushbuttons 130.

In a similar manner the microprocessor 300 in the secondary infusion module 40 activates and controls the display 42. The microprocessor 300 receives secondary solution drop detection information from the integral secondary drop detector 102 and level detector 106, in particular drop detection and high or low level information, as well as notification that the drip chamber 81 has been properly mounted. The Load key 88, the Infuse key 90, the SELECT pushbutton 82, the STANDBY pushbutton 84, and the up/down pushbuttons 86 also are connected to provide inputs to the microprocessor 300.

The two microprocessors are interconnected by a 6-line communications bus 250, enclosed within the cable 34. The six lines include a transmit line, a receive line, a clock line, a $V_{cc}$ regulated voltage line, a $V_{batt}$ battery voltage line, and a ground line. During data transmission data words between the two microprocessors are sent and received by transceivers, one of which is located in the interface 32 at the bottom of the primary controller. A second transceiver is located in the secondary infusion module 40. Redundant transmissions are employed to assure data integrity.

An infusion procedure may be commenced using the system of the present invention by starting to administer the secondary solution first, then changing over to administration of the primary solution. One advantage of the arrangement of the present invention is that secondary solution administration can be commenced while the administration of primary solution is in progress, whereafter the system will revert back to primary solution administration when the administration of secondary solution is completed. Operation of the system of the present invention will be illustrated by explaining the latter process.

To begin administration of a primary solution, the container is suspended from the pole, and the primary administration set (including drip chamber 26, tubing section 8, check valve 6, Y-connector 10, tubing section 12, pinch valve 22, 79 or cassette 50, and tubing section 14) is connected to the solution container and primed with solution. With the administration set clamped shut the primary controller is programmed by entering values for the total dose in ml and the flow rate in ml/hr, using the SELECT pushbutton 134 and the up/down pushbuttons 130. As the values are entered they are verified visually on the primary display 28. When the primary solution values are properly entered the clamp on the tubing set is released and the infuse pushbutton 138 is depressed to begin infusion. The microprocessor 200 will thereupon execute a series of hardware and software checks to verify that the system is connected and operating properly, and will begin to control the pump or precision valve mechanism to adjust for the desired flow rate. As the infusion proceeds, information on the rate of progress is displayed on the primary display 28.

The administration of primary solution may be interrupted by the administration of the secondary solution as follows. A hook which is a part of the secondary administration set is used to suspend the primary solution container from the pole at a level below that of the secondary solution container. The secondary solution container is suspended from the pole and the secondary administration set (including the secondary drip chamber 81 and the tubing line 16) is connected to the container and primed with solution. The tubing line 16 is clamped and a needle at the end of tubing section 16 is inserted into the Y-connector 10. The secondary infusion module 40 is mounted about the secondary drip chamber 81 by inserting the drip chamber 81 into the cavity at the side of the module while depressing then releasing the Load key. The module is then programmed for the values of secondary solution delivery by depressing the SELECT pushbutton 82 and the up/down pushbuttons 86. Entry of the correct values is visually confirmed by viewing the display 42 on the module. The clamp on the administration set is released and delivery of the secondary solution begun by depressing the Infuse key on the module.

As soon as the secondary infusion module is connected to the primary controller, power is provided to the module 40 from the primary controller and the microprocessors in the two units begin exchanging status bytes of information. During this period of initialization the secondary microprocessor 300 executes a series of hardware and software checks to assure that the secondary system is connected and operating properly. Once the Infuse key has been depressed, an intense burst of communication between the two microprocessors begins. The microprocessor 300 sends a burst of twelve 8-bit bytes to the microprocessor 200 over the communications bus 250. This data burst informs the primary controller as to the infusion parameters to be used for controlling the dose and flow rate. The received data is echoed back to the module for verification and the primary microprocessor begins to adjust the flow control mechanism for the proper rate of fluid delivery of the secondary solution. After the flow rate has been set, the two microprocessors resume exchanging status information at a low level. The primary controller sends eight-bit bytes to the secondary microprocessor 300, each byte containing a "dose decrement" bit, a primary alarm bit, a "stop infuse" bit, and an unused bit. These four bits are repeated in the last four bits of the byte for redundancy checking. Delivery of the secondary solution commences as the pressure head of the secondary solution closes the check valve 6 and the secondary solution flows into the pump or control valve mechanism.

During delivery of the secondary solution the microprocessor 300 monitors the drop formation and fluid level in the secondary drip chamber 81. Every eight milliseconds the secondary microprocessor 81 transmits an 8-bit status byte to the primary microprocessor. Each byte contains an alarm bit, a drop sense bit, a start/stop bit, and a level bit. These four bits are replicated in the second four bits of the byte for redundancy. Whenever a falling drop is detected in the secondary drip chamber the drop sense bit is set in the transmitted byte, and held for 100 milliseconds for debounce purposes. The start/stop bit is set and held after the Infuse key is depressed, and is released only when secondary infusion is completed. When this bit is released, the secondary infusion module is shut down and the infusion of primary solution resumes. The other bits in the status byte, including the alarm bit and the level bit, are checked by the primary microprocessor 200 every 72 milliseconds. The level bit is set if the secondary microprocessor detects the presence of fluid at the level of detector 106, 106' in the secondary drip chamber 81. This may or may not be an error condition, depending upon the status of the drop sense bit: if both bits are set for 100 msec, a falling drop has been detected; if both bits remain set for more than two seconds, the drip chamber is filled with solution and an alarm occurs; if both bits are not set, there is a low solution level in the drip chamber and the module will continue to await the detection of a falling droplet; if the level bit is not set and the drop sense bit is intermittent, drops are occurring in an insufficiently filled drip chamber; if the level bit is not set and the drop sense bit is continuously set there is no drip chamber in the module 40; and if the level bit is continuously set and the drop sense bit is continuously not set, the drip chamber 81 and secondary administration set are primed and awaiting the infuse command.

When a secondary drip chamber fault is detected, the alarm on the primary controller sounds, the system shuts down, and the primary controller displays "SECONDRY" on its message center. The exact type of fault is displayed on the secondary infusion module's message center. A flow-related error would be detected by the primary controller, since the primary controller is operating and monitoring the flow-regulating mechanism. When a flow-related error is detected, the system is shut down as the alarm sounds, and the error type is displayed on the message center of the primary controller.

When the secondary infusion module is delivering the secondary solution, either after interrupting primary solution delivery or by starting the system with initial delivery of the secondary solution, there are several ways of terminating secondary solution delivery. One way is to deliver the programmed dose of secondary solution, whereupon system operation switches over from the secondary module to the primary controller. It is possible to deliver not just a measured dose, but the entire supply of secondary solution. The module is programmed to do this by decrementing from a dose of "000" using the up/down keys, whereupon the dose display reads "ALL." The delivery of the full supply of solution is detected by a low level detection in the secondary drip chamber.

There are also three types of alarm conditions which will terminate secondary solution delivery. One is an error condition in the secondary drip chamber, which is detected by the secondary module and communicated to the primary controller. A second type, as mentioned above, is a flow-related error which is detected by the primary controller. The third type of error is a hardware or software malfunction or communication link problem, which may be detected by either the primary controller or the secondary module.

Finally, it is possible to stop secondary solution delivery by depressing the STANDBY pushbuttons 84 or 136. This will stop the delivery of the secondary solution and switch the system over to the delivery of the primary solution. The STANDBY pushbutton 84 is also depressed following a secondary error detection to clear the secondary alarm state as the error condition is remedied. Secondary solution delivery may be restarted after the STANDBY pushbutton is activated by again depressing the Infuse key.

The dual source infusion system of FIG. 1 may be operated by first suspending the solution containers from the pole. The primary administration set is connected to the primary solution container and is primed with solution and clamped. The secondary administration set is connected to the secondary solution container, primed, clamped, and connected to the Y-connector of the primary administration set. The primary controller 20 is programmed for delivery of the primary solution by entering the flow rate, dose, and any other information necessary such as the fluid code. As these values are programmed into the controller with the pushbuttons 30 they may be visually verified on the display 28. The secondary infusion module 40 is then programmed for delivery of the secondary solution using the pushbuttons 44 on the module. The values for the dose and flow rate of the secondary solution can be observed directly on the module display 42 as they are entered. When both units are programmed the delivery of the secondary solution is commenced by depressing the Infuse key. As fluid delivery continues, the progress of secondary fluid delivery can be seen immediately on the module disPlay 42, and the programmed values for the primary solution can be checked by viewing them on the primary controller display 28. When the programmed dose of secondary solution has been delivered, the total volume of solution delivered can be viewed on the controller display and the volume of primary solution remaining to be delivered can be simultaneously viewed on the controller display. Information as to the delivery of both solutions is thus readily and unambiguously apparent to the user without any manipulation of either the module or the controller.

What is claimed is:

1. A dual source parenteral infusion system comprising:
    a source of primary parenteral solution;
    a source of secondary parenteral solution;
    a primary administration set connected to said primary solution source, including a Y-connector and a section of common tubing;
    a secondary administration set connected to said secondary solution source and to said Y-connector and including a secondary drip chamber;
    a primary controller, including flow control means connected to said common tubing, means for detecting the delivery of primary solution, a display for displaying fluid delivery parameters, and means for programming said controller with fluid delivery parameters;
    a secondary infusion module, separable from said primary controller and communicating with said primary controller, operating in conjunction with said secondary drip chamber, and adapted for connection with said secondary administration set, and including a display for displaying fluid delivery parameters of said secondary solution; and
    wherein said secondary infusion module further includes means for communicating information concerning the operation of said secondary chamber to said primary controller.

2. The dual source parenteral infusion system of claim 1, wherein said secondary infusion module further includes means for programming said module with fluid delivery parameters of said secondary solution.

3. The dual source parenteral infusion system of claim 2, wherein said secondary infusion module further includes means for initiating the delivery of said secondary solution.

4. The dual source parenteral infusion system of claim 3, wherein said secondary infusion module further includes a drop detector connected to said secondary drip chamber.

5. The dual source parenteral infusion system of claim 4, wherein said module display includes means for displaying errors concerning the delivery of said secondary solution.

6. The dual source parenteral infusion system of claim 5, wherein said means for displaying errors displays errors concerning the operation of said secondary drip chamber.

7. The dual source parenteral infusion system of claim 6, wherein said primary controller display includes means for displaying flow-related errors.

8. The dual source parenteral infusion system of claim 3, wherein said secondary infusion module further includes means for selectively occluding said secondary administration set.

9. A dual source parenteral infusion system, including primary and secondary administration sets for administering solutions from primary and secondary solution sources, said administration sets being connected to a common tubing line, a fluid delivery rate controller connected to said common tubing line, said system further comprising:
    a secondary infusion module adapted for connection to said secondary administration and communicating with said controller, said module including means for detecting the delivery of said secondary solution and means for displaying parameters associated with the delivery of said secondary solution; and
    wherein said secondary administration set includes a secondary drip chamber, and wherein said detecting means includes a drop detector connected to said secondary drip chamber.

10. The dual source parenteral infusion system of claim 9, wherein said secondary infusion module includes means for programming said module with values associated with the delivery of said secondary solution.

11. The dual source parenteral infusion system of claim 10, wherein said secondary infusion module includes a unitary housing, and said housing includes said drop detector, said displaying means, and said programming means.

12. The dual source parenteral infusion system of claim 11, wherein said housing is mounted about said secondary drip chamber.

13. A dual source parenteral infusion system, including primary and secondary administration sets for administering solutions from primary and secondary solution sources, said administration sets being connected to a common tubing line, a fluid delivery rate controller connected to said common tubing line, said system further comprising:
 a secondary infusion module associated with said secondary administration set and communicating with said controller, said module including means for detecting the delivery of said secondary solution and means for displaying parameters associated with the delivery of said secondary solution;
 wherein said secondary infusion module includes means for programming said module with values associated with the delivery of said secondary solution;
 wherein said secondary administration set includes a secondary drip chamber, and wherein said detecting means includes a drop detector connected to said secondary drip chamber; and
 wherein said secondary infusion module further includes means for transmitting information about the operation of said secondary drip chamber to said controller, and wherein said controller includes means for transmitting information about the rate of fluid delivery to said secondary infusion module.

14. The dual source parenteral infusion system of claim 13, wherein said information about the operation of said secondary drip chamber includes drop detection and solution level information, and wherein said information about the rate of fluid delivery includes information as to the delivered dose of solution,
 wherein said delivered dose information is displayed on said displaying means.

15. The dual source parenteral infusion system of claim 13, wherein said transmitting means of said secondary infusion module transmits delivery rate and dose information to said fluid delivery rate controller prior to commencement of secondary solution administration.

* * * * *

UNITED STATES PATENT AND TRADEMARK OFFICE
CERTIFICATE OF CORRECTION

PATENT NO. : 4,946,439

DATED : August 7, 1990

INVENTOR(S) : Philip N. Eggers and Hal C. Danby

It is certified that error appears in the above-identified patent and that said Letters Patent is hereby corrected as shown below:

On the title page item [75] Inventors: insert --Hal C. Danby--.

Signed and Sealed this

Third Day of March, 1992

Attest:

HARRY F. MANBECK, JR.

Attesting Officer

Commissioner of Patents and Trademarks